US008877293B2

United States Patent
Evans et al.

(10) Patent No.: US 8,877,293 B2
(45) Date of Patent: Nov. 4, 2014

(54) SILICONE GUM EMULSIONS

(75) Inventors: Steven Mark Evans, Freeland, MI (US);
Donald Taylor Liles, Midland, MI (US);
Mustafa A. Mohamed, Quincy, MA (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 13/813,208

(22) PCT Filed: Aug. 2, 2011

(86) PCT No.: PCT/US2011/046174
§ 371 (c)(1),
(2), (4) Date: Jan. 30, 2013

(87) PCT Pub. No.: WO2012/018750
PCT Pub. Date: Feb. 9, 2012

(65) Prior Publication Data
US 2013/0122204 A1  May 16, 2013

Related U.S. Application Data

(60) Provisional application No. 61/370,119, filed on Aug. 3, 2010, provisional application No. 61/512,966, filed on Jul. 29, 2011.

(51) Int. Cl.
*B01F 3/00* (2006.01)
*C09D 183/04* (2006.01)
*A61Q 19/00* (2006.01)
*B01F 17/00* (2006.01)
*B01F 17/54* (2006.01)
*A61K 8/86* (2006.01)
*A61K 8/90* (2006.01)
*C08J 3/05* (2006.01)
*A61K 8/892* (2006.01)
*A61K 8/898* (2006.01)
*C08G 77/16* (2006.01)

(52) U.S. Cl.
CPC . *B01F 3/00* (2013.01); *A61Q 19/00* (2013.01); *B01F 17/0028* (2013.01); *B01F 17/0071* (2013.01); *C08J 2383/04* (2013.01); *C08G 77/16* (2013.01); *A61K 2800/594* (2013.01); *A61K 8/86* (2013.01); *A61K 8/90* (2013.01); *C08J 3/05* (2013.01); *C09D 183/04* (2013.01); *A61K 8/892* (2013.01); *A61K 8/898* (2013.01)

USPC .......... 427/372.2; 424/78.03; 424/70.12; 514/772.3; 524/500

(58) Field of Classification Search
None
See application file for complete search history.

(56) References Cited

U.S. PATENT DOCUMENTS

| 4,125,470 | A | | 11/1978 | Fenton et al. | |
|---|---|---|---|---|---|
| 4,347,333 | A | * | 8/1982 | Lohr et al. | 524/269 |
| 4,724,851 | A | * | 2/1988 | Cornwall et al. | 132/203 |
| 4,842,766 | A | * | 6/1989 | Blehm et al. | 516/23 |
| 5,057,306 | A | | 10/1991 | Hill et al. | |
| 5,100,657 | A | * | 3/1992 | Ansher-Jackson et al. | 424/70.12 |
| 5,302,658 | A | * | 4/1994 | Gee et al. | 524/732 |
| 5,538,667 | A | | 7/1996 | Hill et al. | |
| 5,632,998 | A | * | 5/1997 | Midha et al. | 424/401 |
| 5,645,841 | A | * | 7/1997 | Hill et al. | 424/401 |
| 5,759,208 | A | * | 6/1998 | Zhen et al. | 8/137 |
| 6,531,229 | B1 | * | 3/2003 | Franzoni et al. | 428/447 |
| 6,635,702 | B1 | * | 10/2003 | Schmucker-Castner et al. | 524/291 |
| 7,183,243 | B2 | * | 2/2007 | Ainger et al. | 510/121 |
| 7,399,350 | B2 | * | 7/2008 | Rajaraman et al. | 106/31.59 |
| 7,727,941 | B2 | * | 6/2010 | Morrison et al. | 508/144 |
| 2004/0234475 | A1 | * | 11/2004 | Lannibois-Drean et al. | 424/70.12 |
| 2005/0169864 | A1 | * | 8/2005 | Derici et al. | 424/70.11 |
| 2006/0057097 | A1 | * | 3/2006 | Derici et al. | 424/70.122 |
| 2007/0107747 | A1 | | 5/2007 | Hill et al. | |
| 2007/0203263 | A1 | * | 8/2007 | Schroeck et al. | 523/322 |
| 2011/0059143 | A1 | * | 3/2011 | Iavarone et al. | 424/401 |
| 2012/0157312 | A1 | * | 6/2012 | Krapp et al. | 504/206 |

FOREIGN PATENT DOCUMENTS

| EP | 0739929 | 10/1996 |
|---|---|---|
| WO | 2009077389 | 6/2009 |

* cited by examiner

*Primary Examiner* — Robert S Loewe

(74) *Attorney, Agent, or Firm* — Baltazar Gomez; Alan Zombeck

(57) ABSTRACT

A process for preparing emulsions of silicone gums is disclosed based on using an ethylene oxide/propylene oxide block copolymer as the emulsifier. The emulsions produced by the present process are useful as coatings additives for both water-based and oil-based coatings to obtain improved slip and anti-mar properties. The emulsions may also be used in the manufacture of tires as band ply lubricants. They may also be used in personal care applications.

12 Claims, No Drawings

SILICONE GUM EMULSIONS

CROSS-REFERENCE TO RELATED APPLICATIONS

This application is a U.S. national stage filing under 35 U.S.C. §371 of PCT Application No. PCT/US11/46174 filed on Aug. 20, 2011, which claims the benefit of U.S. Provisional Patent Application No. 61/370,119 filed Aug. 3, 2010 and U.S. Provisional Patent Application No. 61/512,966 filed Jul. 29, 2011 under 35 U.S.C. §119 (e). PCT Application No. PCT/US11/46174 and U.S. Provisional Patent Application No. 61/370,119 and U.S. Provisional Patent Application No. 61/512,966 are hereby incorporated by reference.

BACKGROUND OF THE INVENTION

Silicone gums generally consist of linear chains of poly (dimethylsiloxane) that typically possess kinetic viscosities greater than one million cSt at 25° C. Silicone gum emulsions are important in the coatings industry as they function as slip and anti-mar additives for both aqueous and non-aqueous coatings. An important industrial application of silicone gum emulsions is as "band ply lubricants," used in the manufacture of tires.

Preparation of aqueous mechanical emulsions of silicone gum is difficult due to the handling of such highly viscous materials. These emulsions are typically prepared using a specialized surfactant based on a siloxane copolymer resin. U.S. Pat. No. 4,125,470 to Fenton and Keil describes representative emulsions of this type. A drawback to these types of emulsions is that they contain xylene and other undesirable substances that are present during the manufacture of the siloxane copolymer resin. The presence of xylene in the band ply lube products also precludes their use in personal care applications.

Silicone gum can be emulsified using specialized equipment such as a twin screw extruder (TSE). However, the costs for such equipment are relatively high, both from a capital and an operational standpoint.

Thus, there exists a need to identify processes to prepare mechanical emulsions of silicone gums that do not require specialized surfactants containing aromatic solvents, nor require expensive emulsification equipment.

BRIEF SUMMARY OF THE INVENTION

The present inventors have discovered that mechanical emulsions of silicone gums may be readily prepared in simple equipment using a specific class of certain nonionic surfactants, namely poly(oxyethylene)-poly(oxypropylene)-poly(oxyethylene) block copolymers. The resulting emulsions are free of aromatic solvents, that are typically found in many of the current commercial silicone gum emulsion products. The present emulsions are useful as additives in various personal and household care formulations. The present emulsions are also useful additives in various coating and ink formulations. In particular, the coefficient of friction of coatings or ink compositions containing the present emulsions may be improved vs conventional silicone gum emulsions.

The present disclosure relates to a process for making a silicone gum emulsion comprising:
I) forming a dispersion of;
  A) 100 parts of a silicone gum,
  B) 5 to 100 parts of a ethylene oxide/propylene oxide block copolymer,
II) admixing a sufficient amount of water to the dispersion from step I) to form an emulsion,
III) optionally, further shear mixing the emulsion.

DETAILED DESCRIPTION OF THE INVENTION

Step I of the present process involves forming a dispersion of;
  A) 100 parts of a silicone gum, and
  B) 5 to 100 parts of a ethylene oxide/propylene oxide block copolymer.

As used herein, "parts" refers to parts by weight.

A) The Silicone Gum

Component A) is a silicone gum. "Silicone gum" as used herein refers to predominately linear organopolysiloxanes having sufficiently high molecular weight (Mw) to provide kinetic viscosities greater than 500 thousand cSt at 25° C. While any organopolysiloxane considered as a gum may be selected as component (A), typically the silicone gum is a diorganopolysiloxane gum with a molecular weight sufficient to impart a William's plasticity number of at least about 30 as determined by the American Society for Testing and Materials (ASTM) test method 926. The silicon-bonded organic groups of the diorganopolysiloxane may independently be selected from hydrocarbon or halogenated hydrocarbon groups. These may be specifically exemplified by alkyl groups having 1 to 20 carbon atoms, such as methyl, ethyl, propyl, butyl, pentyl and hexyl; cycloalkyl groups, such as cyclohexyl and cycloheptyl; aryl groups having 6 to 12 carbon atoms, such as phenyl, tolyl and xylyl; aralkyl groups having 7 to 20 carbon atoms, such as benzyl and phenylethyl; and halogenated alkyl groups having 1 to 20 carbon atoms, such as 3,3,3-trifluoropropyl and chloromethyl. Thus, diorganopolysiloxane can be a homopolymer, a copolymer or a terpolymer containing such organic groups. Examples include homopolymers comprising dimethylsiloxy units, homopolymers comprising 3,3,3-trifluoropropylmethylsiloxy units, copolymers comprising dimethylsiloxy units and phenylmethylsiloxy units, copolymers comprising dimethylsiloxy units and 3,3,3-trifluoropropylmethylsiloxy units, copolymers of dimethylsiloxy units and diphenylsiloxy units and interpolymers of dimethylsiloxy units, diphenylsiloxy units and phenylmethylsiloxy units, among others.

The silicon-bonded organic groups of the diorganopolysiloxane may also be selected from alkenyl groups having 1 to 20 carbon atoms, such as vinyl, allyl, butyl, pentyl, hexenyl, or dodecenyl. Examples include; dimethylvinylsiloxy-endblocked dimethylpolysiloxanes; dimethylvinylsiloxy-endblocked dimethylsiloxane-methylvinylsiloxane copolymers; dimethylvinylsiloxy-endblocked methylphenylpolysiloxanes; dimethylvinylsiloxy-endblocked methylphenylsiloxane-dimethylsiloxane-methylvinylsiloxane copolymers.

The silicon-bonded organic groups of the diorganopolysiloxane may also be selected from various organofunctional groups such as amino, amido, mercapto, or epoxy functional groups.

The molecular structure is also not critical and is exemplified by straight-chain and partially branched straight-chain structures, the linear systems being the most typical.

The silicone gum used as component A) may also be a combination or mixture of any of the aforementioned polydiorganosiloxanes.

In one embodiment, the silicone gum is a hydroxy terminated polydimethylsiloxane gum having a viscosity of at least 20 million cP at 25° C. at 0.01 Hz.

The silicone gum may be used in combination with other organopolysiloxanes. Organopolysiloxanes are polymers containing siloxane units independently selected from ($R_3SiO_{1/2}$), ($R_2SiO_{2/2}$), ($RSiO_{3/2}$), or ($SiO_{4/2}$) siloxy units, where R may be any monovalent organic group. When R is a methyl group in the ($R_3SiO_{1/2}$), ($R_2SiO_{2/2}$), ($RSiO_{3/2}$), or ($SiO_{4/2}$) siloxy units of an organopolysiloxane, the siloxy units are commonly referred to as M, D, T, and Q units respectively. These siloxy units can be combined in various manners to form cyclic, linear, or branched structures. The chemical and physical properties of the resulting polymeric structures can vary. For example organopolysiloxanes can be volatile or low viscosity fluids, high viscosity fluids/gums, elastomers or rubbers, and resins depending on the number and type of siloxy units in the average polymeric formula. R may be any monovalent organic group, alternatively R is a hydrocarbon group containing 1 to 30 carbons, alternatively R is an alkyl group containing 1 to 30 carbon atoms, or alternatively R is methyl.

The amount of the additional organopolysiloxane combined with the silicone gum may vary. Typically, 0.1 parts to 1000 parts by weight, alternatively 0.1 to 100 parts by weight of the additional organopolysiloxane is added for every 100 parts of the silicone gum.

In one embodiment, the silicone gum is combined with an aminofunctional organopolysiloxane. The aminofunctional organopolysiloxanes may be characterized by having at least one of the R groups in the formula $R_nSiO_{(4-n)/2}$ be an amino functional group. The amino functional group may be present on any siloxy unit having an R substituent, that is, they may be present on any ($R_3SiO_{1/2}$), ($R_2SiO_{2/2}$), or ($RSiO_{3/2}$) unit, and is designated in the formulas herein as $R^N$. The amino-functional organic group $R^N$ is illustrated by groups having the formula; $-R^3NHR^4$, $-R^3NR_2^4$, or $-R^3NHR^3NHR^4$, wherein each $R^3$ is independently a divalent hydrocarbon group having at least 2 carbon atoms, and $R^4$ is hydrogen or an alkyl group. Each $R^3$ is typically an alkylene group having from 2 to 20 carbon atoms. $R^3$ is illustrated by groups such as; $-CH_2CH_2-$, $-CH_2CH_2CH_2-$, $-CH_2CHCH_3-$, $-CH_2CH_2CH_2CH_2-$, $-CH_2CH(CH_3)CH_2-$, $-CH_2CH_2CH_2CH_2CH_2-$, $-CH_2CH_2CH_2CH_2CH_2CH_2-$, $-CH_2CH_2CH(CH_2CH_3)CH_2CH_2CH_2-$, $-CH_2CH_2CH_2CH_2CH_2CH_2CH_2CH_2-$, and $-CH_2CH_2CH_2CH_2CH_2CH_2CH_2CH_2CH_2CH_2-$. The alkyl groups $R^4$ are as illustrated above for R. When $R^4$ is an alkyl group, it is typically methyl.

Some examples of suitable amino-functional hydrocarbon groups are; $-CH_2CH_2NH_2$, $-CH_2CH_2CH_2NH_2$, $-CH_2CH(CH_3)NH_2$, $-CH_2CH_2CH_2CH_2NH_2$, $-CH_2CH_2CH_2CH_2CH_2NH_2$, $-CH_2CH_2CH_2CH_2CH_2CH_2NH_2$, $-CH_2CH_2NHCH_3$, $-CH_2CH_2CH_2NHCH_3$, $-CH_2CH(CH_3)CH_2NHCH_3$, $-CH_2CH_2CH_2CH_2NHCH_3$, $-CH_2CH_2NHCH_2CH_2NH_2$, $-CH_2CH_2CH_2NHCH_2CH_2NH_2$, $-CH_2CH_2CH_2NHCH_2CH_2CH_2NH_2$, $-CH_2CH_2CH_2CH_2NHCH_2CH_2CH_2NH_2$, $-CH_2CH_2NHCH_2CH_2NHCH_3$, $-CH_2CH_2CH_2NHCH_2CH_2CH_2NHCH_3$, $-CH_2CH_2CH_2CH_2NHCH_2CH_2CH_2CH_2NHCH_3$, and $-CH_2CH_2NHCH_2CH_2NHCH_2CH_2CH_3$.

Alternatively, the amino functional group is $-CH_2CH(CH_3)CH_2NHCH_2CH_2NH_2$.

The aminofunctional organopolysiloxane used in combination with the silicone gum may be selected from those having the average formula;

where; a is 1-1000, alternatively 1 to 500, alternatively 1 to 200, b is 1-100, alternatively 1 to 50, alternatively 1 to 10,
R is independently a monovalent organic group,
alternatively R is a hydrocarbon containing 1-30 carbon atoms,
alternatively R is a monovalent alkyl group containing 1-12 carbons, or alternatively R is a methyl group;
$R^N$ is as defined above.

The aminofunctional organopolysiloxane used I combination with the silicone gum may also be a combination of any of the aforementioned aminofunctional organopolysiloxanes.

B) The Ethylene Oxide/Propylene Oxide Block Copolymer

Component B) is an ethylene oxide/propylene oxide block copolymer. Component B) may be selected from those ethylene oxide/propylene oxide block copolymers known to have surfactant behavior. Typically, the ethylene oxide/propylene oxide block copolymers useful as component B) are surfactants having an HLB of at least 12, alternatively, at least 15, or alternatively at least 18.

The molecular weight of the ethylene oxide/propylene oxide block copolymer may vary, but typically is at least 4,000 g/mol, alternatively at least 8,000 g/mol, or at least 12,000 g/mol.

The amounts of ethylene oxide (EO) and propylene oxide (PO) present in the ethylene oxide/propylene oxide block copolymer may vary, but typically, the amount of EO may vary from 50 percent to 80 percent, or alternatively from 60 percent to about 85 percent, or alternatively from 70 percent to 90 percent.

In one embodiment, component B) is a poly(oxyethylene)-poly(oxypropylene)-poly(oxyethylene) tri-block copolymer. Poly(oxyethylene)-poly(oxypropylene)-poly(oxyethylene) tri-block copolymers are also commonly known as Poloxamers. They are nonionic triblock copolymers composed of a central hydrophobic chain of polyoxypropylene (poly(propylene oxide)) flanked by two hydrophilic chains of polyoxyethylene (poly(ethylene oxide)).

Poly(oxyethylene)-poly(oxypropylene)-poly(oxyethylene) tri-block copolymers are commercially available from BASF (Florham Park, N.J.) and are sold under the tradename PLURONIC®. Representative, non-limiting examples suitable as component (B) include; PLURONIC® F127, PLURONIC® F98, PLURONIC® F88, PLURONIC® F87, PLURONIC® F77 and PLURONIC® F68, and PLURONIC® F-108.

In a further embodiment, the poly(oxyethylene)-poly(oxypropylene)-poly(oxyethylene) tri-block copolymer has the formula;

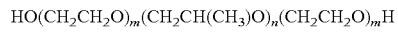

where the subscript "m" may vary from 50 to 400, or alternatively from 100 to 300,
and the subscript "n" may vary from 20 to 100, or alternatively from 25 to 100.

In one embodiment, component B) is a tetrafunctional poly(oxyethylene)-poly(oxypropylene) block copolymer derived from the sequential addition of propylene oxide and ethylene oxide to ethylene diamine. These tetra-functional block copolymers are also commonly known as Poloxamines. The tetrafunctional poly(oxyethylene)-poly(oxypropylene) block copolymer may have the average formula;

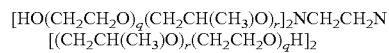

where the subscript "q" may vary from 50 to 400, or alternatively from 100 to 300,
and the subscript "r" may vary from 15 to 75, or alternatively from 20 to 50.

Tetrafunctional poly(oxyethylene)-poly(oxypropylene) block copolymers are commercially available from BASF (Florham Park, N.J.) and are sold under the tradename TETRONIC®. Representative, non-limiting examples suitable as component (B) include; TETRONIC® 908, TETRONIC® 1107, TETRONIC® 1307, TETRONIC® 1508 and TETRONIC® 1504.

The amount of components A) and B) combined in step I) are as follows;

A) 100 parts of a silicone gum, and

B) 5 to 100 parts, alternatively 10 to 40 parts, or alternatively 10 to 25 of the ethylene oxide/propylene oxide block copolymer.

In one embodiment, the dispersion formed in step I) consists essentially of components A) and B) as described above. In this embodiment, no additional surfactants or emulsifiers are added in step I). Furthermore, no solvents are added for the purpose of enhancing formation of an emulsion. As used herein, the phrase "essentially free of "solvents" means that solvents are not added to components A) and B) in order to create a mixture of suitable viscosity that can be processed on typical emulsification devices. More specifically, "solvents" as used herein is meant to include any water immiscible low molecular weight organic or silicone material added to the non-aqueous phase of an emulsion for the purpose of enhancing the formation of the emulsion, and is subsequently removed after the formation of the emulsion, such as evaporation during a drying or film formation step. Thus, the phrase "essentially free of solvent" is not meant to exclude the presence of solvent in minor quantities in process or emulsions of the present invention. For example, there may be instances where the components A) and B) may contain minor amounts of solvent as supplied commercially. Small amounts of solvent may also be present from residual cleaning operations in an industrial process. Preferably, the amount of solvent present in the premix should be less than 2% by weight of the mixture, and most preferably the amount of solvent should be less than 1% by weight of the mixture.

The dispersion of step (I) may be prepared by combining components A) and B) and further mixing the components to form a dispersion. The resulting dispersion may be considered as a homogenous mixture of the two components. The present inventors have unexpectedly found that certain ethylene oxide/propylene oxide block copolymers readily disperse with silicone gum compositions, and hence enhance the subsequent formation of emulsion compositions thereof. The present inventors believe other nonionic and/or anionic surfactants, typically known for preparing silicone emulsions, do not form such dispersions or homogeneous mixtures upon mixing with a silicone gum (at least not in the absence of a solvent or other substance to act as a dispersing medium). While not wishing to be limited to any theory, the inventors believe the discovery of the present ethylene oxide/propylene oxide block copolymers to form such dispersions with silicone gums, provides emulsion compositions of silicone gums without the presence of undesirable solvents, or requiring elaborate handling/mixing techniques.

Mixing can be accomplished by any method known in the art to effect mixing of high viscosity materials. The mixing may occur either as a batch, semi-continuous, or continuous process. Mixing may occur, for example using, batch mixing equipments with medium/low shear include change-can mixers, double-planetary mixers, conical-screw mixers, ribbon blenders, double-arm or sigma-blade mixers; batch equipments with high-shear and high-speed dispersers include those made by Charles Ross & Sons (NY), Hockmeyer Equipment Corp. (NJ); batch mixing equipment such as those sold under the tradename Speedmixer®; batch equipments with high shear actions include Banbury-type (CW Brabender Instruments Inc., NJ) and Henschel type (Henschel mixers America, TX). Illustrative examples of continuous mixers/compounders include extruders single-screw, twin-screw, and multi-screw extruders, co-rotating extruders, such as those manufactured by Krupp Werner & Pfleiderer Corp (Ramsey, N.J.), and Leistritz (NJ); twin-screw counter-rotating extruders, two-stage extruders, twin-rotor continuous mixers, dynamic or static mixers or combinations of these equipments.

The process of combining and mixing components A) and B) may occur in a single step or multiple step process. Thus, components A) and B) may be combined in total, and subsequently mixed via any of the techniques described above. Alternatively, a portion(s) of components A) and B) may first be combined, mixed, and followed by combining additional quantities of either or both components and further mixing. One skilled in the art would be able to select optimal portions of components A) and B) for combing and mixing, depending on the selection of the quantity used and the specific mixing techniques utilized to perform step I) to provide a dispersion of components A) and B).

Step II of the process involves admixing sufficient water to the mixture of step I to form an emulsion. Typically 5 to 700 parts water are mixed for every 100 parts of the step I mixture to form an emulsion. In one embodiment the emulsion formed is a water continuous emulsion. Typically, the water continuous emulsion has dispersed particles of the silicone gum from step I, and having an average particle size less than 150 μm.

The amount of water added in step II) can vary from 5 to 700 parts per 100 parts by weight of the mixture from step I. The water is added to the mixture from step I at such a rate so as to form an emulsion of the mixture of step I. While this amount of water can vary depending on the selection of the amount of silicone gum present and the specific ethylene oxide/propylene oxide block copolymer used, generally the amount of water is from 5 to 700 parts per 100 parts by weight of the step I mixture, alternatively from 5 to 100 parts per 100 parts by weight of the step I mixture, or alternatively from 5 to 70 parts per 100 parts by weight of the step I mixture.

Typically the water is added to the mixture from step I in incremental portions, whereby each incremental portion comprises less than 30 weight % of the mixture from step I and each incremental portion of water is added successively to the previous after the dispersion of the previous incremental portion of water, wherein sufficient incremental portions of water are added to form an emulsion.

Alternatively, a portion or all the water used in step I) may be substituted with various hydrophilic solvents that are soluble with water such as low molecular weight alcohols, ethers, esters or glycols. Representative non-limiting examples include low molecular weight alcohols such as methanol, ethanol, propanol, isopropanol and the like; low molecular weight ethers such as di(propyleneglycol) mono methyl ether, di(ethyleneglycol) butyl ether, di(ethyleneglycol) methyl ether, di(propyleneglycol) butyl ether, di(propyleneglycol) methyl ether acetate, di(propyleneglycol) propyl ether, ethylene glycol phenyl ether, propylene glycol butyl ether, 1-methoxy-2-propanol, 1-methoxy-2-propyl acetate, propylene glycol propyl ether, 1-phenoxy-2-propanol, tri(propyleneglycol) methyl ether and tri(propyleneglycol) butyl ether, and other like glycols.

Mixing in step (II) can be accomplished by any method known in the art to affect mixing of high viscosity materials. The mixing may occur either as a batch, semi-continuous, or continuous process. Any of the mixing methods as described for step (I), may be used to affect mixing in step (II). Typically, the same equipment is used to effect mixing in steps I) and II).

Optionally, the water continuous emulsion formed in step (II) may be further sheared according to step (III) to reduce particle size and/or improve long term storage stability. The shearing may occur by any of the mixing techniques discussed above.

The emulsion products resulting from the present process may be an oil/water emulsion, a water/oil emulsion, a multiple phase or triple emulsion.

In one embodiment, the emulsion products produced by the present process are oil/water emulsions. The oil/water emulsion may be characterized by average volume particle of the dispersed silicone gum (oil) phase in a continuous aqueous phase. The particle size may be determined by laser diffraction of the emulsion. Suitable laser diffraction techniques are well known in the art. The particle size is obtained from a particle size distribution (PSD). The PSD can be determined on a volume, surface, length basis. The volume particle size is equal to the diameter of the sphere that has the same volume as a given particle. The term Dv represents the average volume particle size of the dispersed particles. Dv 50 is the particle size measured in volume corresponding to 50% of the cumulative particle population. In other words if Dv 50=10 μm, 50% of the particle have an average volume particle size below 10 μm and 50% of the particle have a volume average particle size above 10 μm. Dv 90 is the particle size measured in volume corresponding to 90% of the cumulative particle population.

The average volume particle size of the dispersed siloxane particles in the oil/water emulsions is between 0.1 μm and 150 μm; or between 0.1 μm and 30 μm; or between 0.3 μm and 5.0 μm.

Silicone gum content of the present emulsion may vary from 0.5 weight percent to 95 weight percent, alternatively from 20 weight percent to 80 weight percent, or alternatively from 40 weight percent to 60 weight percent.

Additional additives and components may also be included in the emulsion compositions, such as preservatives, freeze/thaw additives, and various thickeners.

The emulsions produced by the present process may be used as coatings additives for both water-based and oil-based coatings to improve slip, coefficient of friction, or anti-mar properties. The emulsions may also be used in the manufacture of tires as band ply lubricants. The emulsions may also be used in antifoam formulations as well as in release compositions.

In one embodiment, the present emulsions are used as an additive in coating compositions containing an acrylic emulsion. The present coating compositions comprise:
  i) 1 to 99 weight percent of an acrylic emulsion;
  alternatively 10 to 99 weight percent of an acrylic emulsion,
  alternatively 50 to 99 weight percent of an acrylic emulsion, or
  alternatively 90 to 99 weight percent of an acrylic emulsion,
  ii) 0.01 to 20 weight percent of a silicone gum emulsion as described above;
  alternatively 0.01 to 20 weight percent of the silicone gum emulsion,
  alternatively 1 to 15 weight percent of the silicone gum emulsion, or
  alternatively 1 to 10 weight percent of the silicone gum emulsion, and
  iii) 0 to 90 weight percent of an organic solvent;
  alternatively 1 to 90 weight percent of an organic solvent,
  alternatively 1 to 50 weight percent of an organic solvent, or
  alternatively 1 to 15 weight percent of an organic solvent.

The present coating compositions contain an acrylic emulsion. As used herein "acrylic emulsions" refer to any water based emulsion of a polyacrylate, polymethacrylate, or other similar copolymers derived from acrylic or methacrylic acid. Many acrylic emulsions are available commercially for ready use in paints and coating formulations. These acrylic emulsions are often described as self-crosslinkable acrylic emulsions, which may be used in the present coating compositions. Representative self-crosslinkable acrylic emulsions include useful in the present compositions include; ALBERDINGK AC 2514, ALBERDINGK AC 25142, ALBERDINGK AC 2518, ALBERDINGK AC 2523, ALBERDINGK AC 2524, ALBERDINGK AC 2537, ALBERDINGK AC 25381, ALBERDINGK AC 2544, ALBERDINGK AC 2546, ALBERDINGK MAC 24, and ALBERDINGK MAC 34 polymer dispersions from Alberdingk Boley, Inc.; EPS 2538 and EPS 2725 acrylic emulsions from EPS Corp.; RHOPLEX™ 3131-LO, RHOPLEX E-693, RHOPLEX E-940, RHOPLEX E-1011, RHOPLEX E-2780, RHOPLEX HG-95P, RHOPLEX HG-700, RHOPLEX HG-706, RHOPLEX PR-33, RHOPLEX TR-934HS, RHOPLEX TR-3349 and RHOPLEX™ VSR-1050 acrylic emulsions from Rohm and Haas Co.; RHOSHIELD™ 636 and RHOSHIELD 3188 polymer dispersions from Rohm and Haas Co; JONCRYL® 8380, 8300, 8211, 1532, 1555, 2560, 1972, 1980, 1982, and 1984 acrylic emulsions from BASF Corp.; NEOCRYL™ A-1127, NEOCRYL A-6115, NEOCRYL XK-12, NEOCRYL XK-90, NEOCRYL XK-98 and NEOCRYL XK-220 acrylic latex polymers from DSM NeoResins, Inc., and mixtures thereof.

In one embodiment, the acrylic emulsion is JONCRYL® 8383 acrylic emulsion from BASF Corp.

The present coating compositions optionally may also contain an organic solvent. The organic solvent may be selected from any organic solvents that are typically used to prepare coating compositions. The organic solvent may include a combination of two or more solvents. When used in the coating compositions, the organic solvent may be present in compositions up to a maximum of 90 weight percent of the composition.

In one embodiment, the organic solvent is a glycol solvent. The glycol solvent helps reduce viscosity and may aid wetting or film coalescence. Representative glycol solvents include ethylene glycol, ethylene glycol methyl ether, ethylene glycol ethyl ether, ethylene glycol monobutyl ether, ethylene glycol-2-ethylhexyl ether, propylene glycol, propylene glycol methyl ether, propylene glycol ethyl ether, propylene glycol monobutyl ether, propylene glycol-2-ethylhexyl ether, diethylene glycol, diethylene glycol methyl ether, diethylene glycol ethyl ether, diethylene glycol monobutyl ether, diethylene ethylhexyl ether, dipropylene glycol, dipropylene glycol methyl ether, dipiopylene glycol ethyl ether, dipiopylene glycol monobutyl ether, dipropylene glycol-2-ethylhexyl ether, and mixtures thereof hydrophilic glycol solvents (e.g., propylene glycol methyl ether or dipropylene glycol monomethyl ether) are preferred.

In one embodiment, the organic solvent is an alcohol. Representative alcohol solvents include both lower molecular weight alcohols; such as methanol, ethanol, propanol, and butanol; as well as branched hydrocarbyl based alcohols like Texanol® solvents; such as 2,2,4-Trimethyl-1,3-pentanediol-mono(2-methylpropanoate).

In a further embodiment, the organic solvent is a combination of a glycol and alcohol, as described above.

The present coating compositions may be prepared by simply combining the components with mixing.

The present disclosure further provides a method of improving the coefficient of friction of a coating comprising; combining the silicone gum emulsions as described above with a coating composition to form a pre-coat mixture, applying a film of the pre-coat mixture to a surface, curing the film to form a coating.

The coating compositions can be any known coating compositions in the art, such as various protective coatings, architectural coatings, or paints. The present silicone gum emulsions may be incorporated into the coating compositions at various amounts by simply mixing the silicone gum emulsion into a pre-formed coating composition. The amount of the silicone gum emulsion may vary, but typically from 0.1 parts by weight of the silicone gum emulsion to 20 parts by weight are used, as based on the total coating composition. The resulting pre-coat mixture may then be applied as a film onto various substrates, and the film cured by any method known in the art. Typically, the films are cured by simply allowing the film to air dry, or alternatively by heating the film.

In one embodiment, the coating composition selected is an ink formulation. Any commercially available ink formulation may be selected.

The present silicone gum emulsions may be formulated into personal care products. The personal care compositions may be in the form of a cream, a gel, a powder, a paste, or a freely pourable liquid. Generally, such compositions can generally be prepared at room temperature if no solid materials at room temperature are present in the compositions, using simple propeller mixers, Brookfield counter-rotating mixers, or homogenizing mixers. No special equipment or processing conditions are typically required. Depending on the type of form made, the method of preparation will be different, but such methods are well known in the art.

The personal care products may be functional with respect to the portion of the body to which they are applied, cosmetic, therapeutic, or some combination thereof. Conventional examples of such products include, but are not limited to: antiperspirants and deodorants, skin care creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers, hair shampoos, hair conditioners, hair colorants, hair relaxants, hair sprays, mousses, gels, permanents, depilatories, and cuticle coats, make-ups, color cosmetics, foundations, concealers, blushes, lipsticks, eyeliners, mascara, oil removers, color cosmetic removers, and powders, medicament creams, pastes or sprays including antiacne, dental hygienic, antibiotic, healing promotive, nutritive and the like, which may be preventative and/or therapeutic. In general the personal care products may be formulated with a carrier that permits application in any conventional form, including but not limited to liquids, rinses, lotions, creams, pastes, gels, foams, mousses, ointments, sprays, aerosols, soaps, sticks, soft solids, solid gels, and gels. What constitutes a suitable carrier is readily apparent to one of ordinary skill in the art.

The compositions according to this invention can be used by the standard methods, such as applying them to the human body, e.g. skin or hair, using applicators, brushes, applying by hand, pouring them and/or possibly rubbing or massaging the composition onto or into the body. Removal methods, for example for color cosmetics are also well known standard methods, including washing, wiping, peeling and the like. For use on the skin, the compositions according to the present invention may be used in a conventional manner for example for conditioning the skin. An effective amount of the composition for the purpose is applied to the skin. Such effective amounts generally range from about 1 $mg/cm^2$ to about 3 $mg/cm^2$. Application to the skin typically includes working the composition into the skin. This method for applying to the skin comprises the steps of contacting the skin with the composition in an effective amount and then rubbing the composition into the skin. These steps can be repeated as many times as desired to achieve the desired benefit.

The use of the compositions according to the invention on hair may use a conventional manner for conditioning hair. An effective amount of the composition for conditioning hair is applied to the hair from any hair conditioning composition such as a shampoo or rinse off conditioner. Such effective amounts generally range from about 0.5 g to about 50 g, preferably from about 1 g to about 20 g. Application to the hair typically includes working the composition through the hair such that most or all of the hair is contacted with the composition. This method for conditioning the hair comprises the steps of applying an effective amount of the hair care composition to the hair, and then working the composition through the hair. These steps can be repeated as many times as desired to achieve the desired conditioning benefit.

EXAMPLES

The following examples are included to demonstrate certain embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. All percentages are in wt. %. All measurements were conducted at 23° C. unless indicated otherwise.

Example 1

Emulsification of Silicone Gum Using Pluronic® F-88

First, 15 g of silicone gum (Dow Corning® SGM-36, a hydroxy terminated polydimethylsiloxane) was weighed into a Max 40 cup along with 1.5 g of Pluronic® F-88 nonionic surfactant and 10 g of 3 mm glass beads. The cup was closed and placed inside a DAC-150 SpeedMixer® and the cup was spun at maximum speed (3450 RPM) for 2 minutes. The cup was opened and the mixture, now very warm, had become a creamy white paste that easily flowed when mixed with a spatula. The walls of the cup were scraped with a spatula and the cup was spun again at maximum speed for 1 minute. Then, 0.88 g of water was added to the cup and the cup was spun for 30 seconds at maximum speed. An additional 1.2 g of water was added and the cup was again spun for 30 seconds at maximum speed. Two more water additions were made, one of 2.5 g and the other 3.92 g with the cup being spun for 20 seconds after each water addition. The milky white mixture was now finished and it consisted of an o/w emulsion of silicone gum having a silicone content of 60 percent by weight. Particle size of the emulsion was determined using a Malvern Mastersizer S (version 2.19) and the results were: Dv50=6.93 um, Dv90=13.24 um.

Example 2

Emulsification of Silicone Gum Using Pluronic® F-108

The following were weighed into a Max 100 cup in the following order: 35 g silicone gum (Dow Corning® SGM 36) having a viscosity of approximately 20 million cP at 0.01 Hz, 16 g of 3 mm spherical glass beads (Fisher) and 7 g of Pluronic® F-108 nonionic surfactant. The cup was closed and placed into a DAC-150 SpeedMixer® and the cup was spun at maximum speed (3450 RPM) for 2 minutes. The cup was opened and the mixture, which had become very warm and had taken on a creamy white, thick paste-like consistency, was stirred by hand using a spatula, with care being taken to scrape the walls and bottom of the Max 100 cup. The cup was closed and spun in the mixer for an additional 1 minute at maximum speed. The mixture was diluted with 28 g of deionized water in 4 increments by adding aliquots of water and spinning the cup for 30 seconds after addition of each aliquot. The increments of water were as follows: 3 g, 5 g, 8 g and 12 g. Following the last dilution, the resulting composition consisted of an o/w emulsion of silicone gum having a silicone content of 50 percent by weight. Particle size of the emulsion was measured using a Malvern® Mastersizer S (Version 2.19) and found to be: Dv50=2.06 μm Dv90=3.35 μm.

Example 3

Emulsification of Silicone Gum using Tetronic® 1107

The following were weighed into a Max 100 cup in the following order: 35 g silicone gum (Dow Corning® SGM 36), 16 g of 3 mm spherical glass beads (Fisher) and 7 g of Tetronic® 1107 nonionic surfactant. The cup was closed and placed into a DAC-150 SpeedMixer® and the cup was spun at maximum speed (3450 RPM) for 2 minutes. The cup was opened and the mixture was stirred by hand using a spatula, with care being taken to scrape the walls and bottom of the Max 100 cup. The cup was closed and spun in the mixer for an additional 1 minute at maximum speed. The mixture was diluted with 28 g of deionized water in 4 increments by adding aliquots of water and spinning the cup for 30 seconds after addition of each aliquot. The increments of water were as follows: 5 g, 5 g, 8 g and 12 g. Following the last dilution, the resulting composition consisted of an o/w emulsion of silicone gum having a silicone content of 50 percent by weight. Particle size of the emulsion was measured using a Malvern® Mastersizer S (Version 2.19) and found to be: Dv50=10.43 μm Dv90=19.13 μm.

Example 4

Emulsification of Silicone Gum using Tetronic® 908

The following were weighed into a Max 100 cup in the following order: 35 g silicone gum (Dow Corning® SGM 36), 16 g of 3 mm spherical glass beads (Fisher) and 7 g of Tetronic®908 nonionic surfactant. The cup was closed and placed into a DAC-150 SpeedMixer® and the cup was spun at maximum speed (3450 RPM) for 2 minutes. The cup was opened and the mixture was stirred by hand using a spatula, with care being taken to scrape the walls and bottom of the Max 100 cup. The cup was closed and spun in the mixer for an additional 1 minute at maximum speed. The mixture was diluted with 28 g of deionized water in 4 increments by adding aliquots of water and spinning the cup for 30 seconds after addition of each aliquot. The increments of water were as follows: 5 g, 5 g, 8 g and 12 g. Following the last dilution, the resulting composition consisted of an o/w emulsion of silicone gum having a silicone content of 50 percent by weight. Particle size of the emulsion was measured using a Malvern® Mastersizer S (Version 2.19) and found to be: Dv50=4.39 μm Dv90=7.97 μm.

Example 5

Emulsification of Silicone Gum+Aminofunctional Silicone Fluid Using Pluronic® F-108

32.4 g of Dow Corning® SGM 36, 3.6 g of Dow Corning® 2-8566 Amino Fluid (an trimethylsiloxy terminated, dimethyl, methyl(aminoethylaminoisobutyl)polysiloxane, having a random distribution of two mole percent of silicon atoms substituted with methyl(aminoethylaminoisobutyl) functionality and of sufficient molecular weight to provide a rotational viscosity of 3,000 mPa·s (cP)), 16 g of 3 mm spherical glass beads and 7.2 g Pluronic® 108 nonionic surfactant were weighed into a Max 100 cup. The cup was closed and placed into a DAC-150 SpeedMixer® and the cup was spun at maximum speed (3450 RPM) for 2 minutes. The cup was opened and the mixture was stirred by hand using a spatula, with care being taken to scrape the walls and bottom of the Max 100 cup. The cup was closed and spun in the mixer for an additional 1 minute at maximum speed. The mixture was diluted with 28 g of deionized water in 4 increments by adding aliquots of water and spinning the cup for 30 seconds after addition of each aliquot. The increments of water were as follows: 5 g, 5 g, 8 g and 12 g. Following the last dilution, the resulting composition consisted of an o/w emulsion of silicone gum having a silicone content of 50 percent by weight. Particle size of the emulsion was measured using a Malvern® Mastersizer 2000 (Version 5.54) and found to be: Dv50=3.17 μm Dv90=5.98 μm.

Example 6

Emulsification of Silicone Gum+$H_2O$-Miscible Organic Solvent Using Pluronic® F-98

35 g of Dow Corning® SGM 36, 16 g of 3 mm spherical glass beads and 8.75 g of Pluronic® F-98 nonionic surfactant were weighed into a Max 100 cup. The cup was closed and placed into a DAC-150 SpeedMixer® and the cup was spun at maximum speed (3450 RPM) for 2 minutes. The cup was opened and the mixture was stirred by hand using a spatula, with care being taken to scrape the walls and bottom of the Max 100 cup. The cup was closed and spun in the mixer for an additional 1 minute at maximum speed. The mixture was diluted with 12 g of deionized water in 3 increments of 4 g each while spinning the cup for 30 seconds at maximum speed after addition of each aliquot. Following the last water addition, 14 g of dipropylene glycol monomethyl ether (Dowanol® DPM) was added in 5 increments: 2 g, 2 g, 3 g, 3 g, 4 g; while spinning the cup for 30 seconds at maximum speed between each addition. The resulting composition consisted of silicone gum dispersed in a water-organic mixture. Particle size was measured using a Malvern® Mastersizer 2000 and found to be: Dv50=2.51 μm, Dv90=27.22 μm.

Example 7

Coatings containing an acrylic emulsion formulation, representative of an industrial paint formulation, were prepared using the following base coating formulation;

| Material | Wt % |
|---|---|
| Joncryl® 8383 | 94 |
| Dowanol® PnB | 4.92 |
| Texanol® | 3 |

Formulations with additives were prepared by adding 0.5% of DC 51 Additive (a commercially available silicone gum emulsion from Dow Corning Corp., Midland, Mich.) or 0.5% of a silicone gum emulsion representative of the present disclosure. (the silicone gum emulsion used in this example was prepared in a similar manner as that of Example 2, but using Pluronic® F-98). Each formulation was coated on Al-panels using a draw down bar. The dried panels was visually inspected and compared to sample without additive. The dynamic coefficient of friction (CoF) was measured for each. In the control experiment (no silicone additive), the CoF of the coating composition alone was found to be greater than 0.4. The coating composition containing DC 51 additive had a CoF of 0.15, whereas the coating composition containing the representative silicone gum emulsion had a CoF of 0.13.

Example 8

A representative silicone gum emulsion (the silicone gum emulsion used in this example was prepared in a similar manner as that of Example 2, but using Plutonic® F-98) was evaluated in a representative ink formulation (a commercial formulation as obtained from Sun Chemical) for its ability to reduce dynamic coefficient of friction (CoF). A comparable formulation was prepared using DC 51 Additive. The ink formulations were coated on paper substrate and CoF measured. The results show that the representative silicone gum emulsion performed better than DC 51 additive for reducing the CoF of the commercial ink formulation. The ink formulation without any additive had a CoF of 0.4, the formulation with DC51 had a CoF of 0.34, whereas the ink formulation containing the representative silicone gum emulsion had a CoF of 0.1.

Comparative Example 1

Attempted Emulsification of Gum Using Pegosperse® 1757-MS

The following were weighed into a Max 100 cup in the following order: 35 g silicone gum (Dow Corning® SGM 36) having a viscosity of approximately 20 million cP at 0.01 Hz, 16 g of 3 mm spherical glass beads (Fisher) and 8 g of Pegosperse® 1757-MS nonionic surfactant (POE 40 monostearate; HLB 18.0). The cup was closed and placed into a SpeedMixer® DAC-150 and the cup was spun at maximum speed (3450 RPM) for 2 minutes. The cup was opened and the mixture, which had become warm, consisted of a single mass of semi-transparent gum with the glass beads being visible within the mass. The white flakes of surfactant were no longer visible. A clear liquid, the melted surfactant, appeared to be present in the cup also, but separate from the mass of silicone polymer. Unlike the Pluronic® surfactants, this surfactant failed to form a dispersion of gum particles in surfactant.

Comparative Example 2

Attempted Emulsification of Gum Using Volpo® L-23

15 g of silicone gum (Dow Corning® SGM 36) having a viscosity of approximately 20 million cP at 0.01 Hz was weighed into a Max 40 cup. This was followed by 1.5 g of Volpo® L-23 nonionic surfactant (lauryl EO-23) and 10 g of 3 mm glass beads. The cup was closed and placed into a DAC-150 SpeedMixer® and the cup was spun at maximum speed (3450 RPM) for 2 minutes. The cup was opened and its contents were inspected. The silicone gum had become a single mass that was slightly opaque and within the mass were the glass beads mostly clumped together. The surfactant appeared to be liquid and the majority of it appeared to be on the surface of the mass of silicone polymer. In other words, most of the surfactant was not dispersed within the silicone. 2 g of water was added to the cup and the cup was spun for 1 minute at maximum speed. The composition now consisted of two phases: a small amount of slightly milky water and a large mass of silicone polymer having the beads incased within the mass. Additional 2 g of water was added and the cup spun again for 1 minute at maximum speed. The results were the same as before with a slightly larger amount of milky water present. This experiment demonstrated that the surfactant Volpo® L-23 also failed to disperse gum.

Comparative Example 3

Attempted Emulsification of Gum Using Genapol® X-080

Using the same procedure as described in Example 2, an attempt was made to prepare an emulsion using 15 g of silicone gum, 1.5 g of Genapol X-080 and 7.5 g of glass beads. The results were the same as in comparative example 2.

Comparative Example 4

Attempted Emulsification of Gum Using Pluronic® F-88+Tergitol® 15-S-9

15 g of SGM-36 was weighed into a Max 40 cup followed by 0.5 g of Pluronic® F-88 and 1.0 g of Tergitol® 15-S-9. 8 g of 3 mm glass beads was added and the cup was closed and spun for 2 minutes at full speed in a DAC-150 SpeedMixer®. The cup was spun again for 1 minute at full speed after which the contents of the cup were inspected. The gum had not dispersed in the surfactant as the gum was slightly opaque and not white when it has dispersed. 2 g of water was added and the cup was spun for 1 minute at full speed. Inspection of the mixture revealed that the water and gum were still in separate phases. In other words, the composition failed to emulsify.

Comparative Example 5

Attempted Emulsification of Gum Using Na Dodecyl Sulfate 15 g of Dow Corning® SGM-36 was weighed into a Max 40 cup followed by 8 g of 3 mm glass beads. 3 g of sodium dodecyl sulfate (Aldrich) was added next and the cup was closed and placed into a DAC 150 SpeedMixer®. The cup was spun for 2 minutes at maximum speed followed by another spin for 1 minute at maximum speed. The composition was completely white, but it had a highly viscous, gum-like consistency. 1 g of water was added and the cup was spun for 1 minute at maximum speed. This was followed by another 1 g of water and an additional 1 g of water for a total of 3 g of water being added, the cup being spun for 1 minute between each water addition. After the final addition of water, the contents of the cup were inspected and found to be essentially gum with surfactant dispersed within and water in a separate phase outside of the gum. In other words, the composition did not form an emulsion.

Comparative Example 6

Attempted Emulsification of Gum Using Arquad® 16-29 Surfactant 15 g of Dow Corning® SGM-36 was weighed into a Max 40 cup followed by 7 g of 3 mm glass beads. 6.2 g of Arquad® 16-29 Surfactant (cetyl trimethylammonium chloride) was added next and the cup was closed and placed into a DAC 150 SpeedMixer®. The cup was spun for 2 minutes at maximum speed. The cup was opened and inspected to find that the gum and surfactant were still in two completely separate phases. In other words, the surfactant did not disperse the gum to any extent.

Comparative Example 7

Attempted Emulsification of Gum Using Pluronic® F-38 Surfactant 15 g of Dow Corning® SGM-36 was weighed into a Max 100 cup followed by 16 g of 3 mm glass beads. 7.2 of Pluronic® F-38 Surfactant was added next and the cup was closed and placed into a DAC 150 SpeedMixer®. The cup was spun for 2 minutes at maximum speed. The cup was opened and inspected to find that the gum and surfactant were still in two completely separate phases. The composition was spun in the DAC 150 SpeedMixer® for an additional 1 minute at maximum speed and the surfactant apparently failed to disperse the silicone such as how Pluronic® F-88 did. Addition of 3 g water followed by spinning in the SpeedMixer® also failed to form an emulsion.

Comparative Example 8

Attempted Emulsification of Gum Using Pluronic® L-35 Surfactant 36 g of Dow Corning® SGM-36 was weighed into a Max 100 cup followed by 16 g of 3 mm glass beads. 7.0 of Pluronic® L-35 Surfactant was added next and the cup was closed and placed into a DAC 150 SpeedMixer®. The cup was spun for 2 minutes at maximum speed. The cup was opened and inspected to find that the gum and surfactant were still in two completely separate phases. The composition was spun in the DAC 150 SpeedMixer® for an additional one minute at maximum speed and the surfactant apparently failed to disperse the silicone such as how Pluronic® F-88 did. Addition of 3 g of water followed by spinning in the SpeedMixer® for one minute also failed to form an emulsion.

Comparative Example 9

Attempted Emulsification of Gum Using Tetronic® 904 Surfactant 36 g of Dow Corning® SGM-36 was weighed into a Max 100 cup followed by 16 g of 3 mm glass beads. 7.2 of Tetronic® 904 Surfactant was added next and the cup was closed and placed into a DAC 150 SpeedMixer®. The cup was spun for 2 minutes at maximum speed. The cup was opened and inspected to find that the gum and surfactant were still in two completely separate phases. The composition was spun in the DAC 150 SpeedMixer® for an additional one minute at maximum speed and there was no change in the appearance of the mixture in the cup. The Tetronic®904 surfactant apparently failed to disperse the silicone such as how Tetronic® 908 did. Addition of 5 g of water followed by spinning in the SpeedMixer® for one minute also failed to form an emulsion.

The invention claimed is:

1. A process for making a silicone gum emulsion comprising:
   I) forming a dispersion consisting essentially of;
      A) 100 parts of a silicone gum,
      B) 5 to 100 parts of a ethylene oxide/propylene oxide block copolymer,
   II) admixing a sufficient amount of water to the dispersion from step I) to form an emulsion,
   III) shear mixing the emulsion to obtain average volume particle size of the dispersed silicone gum particles in the emulsions between 0.1 μm and 150 μm, and wherein no additional surfactants or emulsifiers are added in step I.

2. The process of claim 1 wherein the silicone gum is a hydroxy terminated polydimethylsiloxane having a viscosity of at least 500 thousand cSt at 0.01 Hz at 25° C.

3. The process of claim 1 wherein the ethylene oxide/propylene oxide block copolymer is a poly(oxyethylene)-poly(oxypropylene)-poly(oxyethylene) tri-block copolymer having the formula:

$$HO(CH_2CH_2O)_m(CH_2CH(CH_3)O)_n(CH_2CH_2O)_mH$$

where m vary from 50 to 400,
and n vary from 20 to 100.

4. The process of claim 1 wherein the ethylene oxide/propylene oxide block copolymer is a tetrafunctional poly(oxyethylene)-poly(oxypropylene) block copolymer having the average formula:

$$[HO(CH_2CH_2O)_q(CH_2CH(CH_3)O)_r]_2NCH_2CH_2N$$
$$[(CH_2CH(CH_3)O)_r(CH_2CH_2O)_qH]_2$$

where q vary from 50 to 400, and
r vary from 15 to 75.

5. The process according to claim 1 wherein 5 to 700 parts water are admixed for every 100 parts of the step I dispersion to form the emulsion.

6. The emulsion produced by the process of claim 1.

7. A coating composition containing the emulsion composition of claim 6.

8. The coating composition of claim 6 wherein the coating composition comprises:
   i) 1 to 99 weight percent of an acrylic emulsion,
   ii) 0.01 to 20 weight percent of the silicone gum emulsion of claim 6, and
   iii) 0 to 90 weight percent of an optional organic solvent.

9. A method of improving the coefficient of friction of a coating comprising: combining the emulsion of claim 6 with a coating composition to form a pre-coat mixture, applying a film of the pre-coat mixture to a surface, and curing the film to form a coating.

10. The method of claim 9 wherein the coating composition comprises an acrylic emulsion.

11. The method of claim 9 wherein the coating composition is an ink formulation.

12. A personal care composition containing the emulsion composition of claim 6.

\* \* \* \* \*